(12) United States Patent
Arnin

(10) Patent No.: US 8,241,331 B2
(45) Date of Patent: Aug. 14, 2012

(54) SPINAL IMPLANT HAVING A POST-OPERATIVE ADJUSTABLE DIMENSION

(75) Inventor: Uri Arnin, Kiryat Tivon (IL)

(73) Assignee: Spine21 Ltd., Kiryat Tivon (IL)

( * ) Notice: Subject to any disclaimer, the term of this patent is extended or adjusted under 35 U.S.C. 154(b) by 548 days.

(21) Appl. No.: 11/937,019

(22) Filed: Nov. 8, 2007

(65) Prior Publication Data

US 2009/0125062 A1   May 14, 2009

(51) Int. Cl.
   *A61B 17/70* (2006.01)
(52) U.S. Cl. .................. 606/248; 606/90; 623/17.15
(58) Field of Classification Search .......... 606/247–249, 606/57, 58, 282, 105, 90; 623/17.11–17.16
   See application file for complete search history.

(56) References Cited

U.S. PATENT DOCUMENTS

| | | | | |
|---|---|---|---|---|
| 2,333,033 A * | 10/1943 | Mraz | | 606/57 |
| 4,548,199 A * | 10/1985 | Agee | | 606/57 |
| 4,573,459 A * | 3/1986 | Litton | | 606/58 |
| 4,636,217 A * | 1/1987 | Ogilvie et al. | | 623/17.11 |
| 4,747,394 A * | 5/1988 | Watanabe | | 600/232 |
| 4,827,918 A * | 5/1989 | Olerud | | 606/258 |
| 4,929,247 A * | 5/1990 | Rayhack | | 606/53 |
| 5,097,820 A * | 3/1992 | Shulman et al. | | 600/237 |
| 5,147,358 A * | 9/1992 | Remmler | | 606/57 |
| 5,364,396 A * | 11/1994 | Robinson et al. | | 606/53 |
| 5,405,391 A * | 4/1995 | Hednerson et al. | | 623/17.15 |
| 5,413,602 A * | 5/1995 | Metz-Stavenhagen | | 623/17.15 |
| 5,437,668 A * | 8/1995 | Aronson et al. | | 606/57 |
| 5,458,641 A * | 10/1995 | Ramirez Jimenez | | 623/17.11 |
| 5,601,551 A * | 2/1997 | Taylor et al. | | 606/54 |
| 5,616,117 A * | 4/1997 | Dinkler et al. | | 600/232 |
| 5,895,387 A * | 4/1999 | Guerrero et al. | | 606/71 |
| 5,976,125 A * | 11/1999 | Graham | | 606/32 |
| 6,007,535 A * | 12/1999 | Rayhack et al. | | 606/57 |
| 6,126,660 A * | 10/2000 | Dietz | | 606/90 |
| 6,358,255 B1 * | 3/2002 | Testa | | 606/105 |
| 6,413,231 B1 * | 7/2002 | Berman et al. | | 601/38 |
| 6,454,806 B1 | 9/2002 | Cohen et al. | | |
| 6,508,817 B1 * | 1/2003 | Pensler et al. | | 606/57 |
| 6,616,672 B1 * | 9/2003 | Essiger | | 606/105 |
| 7,011,658 B2 * | 3/2006 | Young | | 606/258 |
| 7,029,472 B1 * | 4/2006 | Fortin | | 606/60 |
| 7,083,650 B2 * | 8/2006 | Moskowitz et al. | | 623/17.11 |
| 2003/0144669 A1 * | 7/2003 | Robinson | | 606/90 |
| 2004/0088054 A1 * | 5/2004 | Berry | | 623/17.11 |
| 2004/0097938 A1 * | 5/2004 | Alleyne | | 606/69 |
| 2005/0004573 A1 * | 1/2005 | Abdou | | 606/61 |
| 2005/0096088 A1 * | 5/2005 | Bae | | 455/558 |
| 2005/0096674 A1 * | 5/2005 | Loshakove et al. | | 606/153 |

(Continued)

FOREIGN PATENT DOCUMENTS

DE   19856013   6/2000

*Primary Examiner* — Eduardo C Robert
*Assistant Examiner* — Jerry Cumberledge
(74) *Attorney, Agent, or Firm* — Dekel Patent Ltd.; David Klein

(57) ABSTRACT

A spinal implant including first spinal attachment member for attaching to a first spinal portion, second spinal attachment member for attaching to a second spinal portion, and a post-implantation variable dimension device disposed between the first and second spinal attachment members, which is operable after completing surgery in which said spinal implant was installed into a patient, to cause relative movement between the first and second spinal attachment members.

4 Claims, 6 Drawing Sheets

U.S. PATENT DOCUMENTS

| | | |
|---|---|---|
| 2005/0165407 A1* | 7/2005 | Diaz .............................. 606/90 |
| 2005/0203534 A1* | 9/2005 | Mommaerts ................... 606/90 |
| 2005/0216017 A1* | 9/2005 | Fielding et al. ................ 606/74 |
| 2005/0234555 A1* | 10/2005 | Sutton et al. ............... 623/17.15 |
| 2005/0240182 A1* | 10/2005 | Zucherman et al. ............ 606/61 |
| 2006/0004447 A1 | 1/2006 | Matrorio et al. |
| 2006/0058790 A1 | 3/2006 | Carl et al. |
| 2006/0085074 A1 | 4/2006 | Raiszadeh |
| 2006/0149385 A1* | 7/2006 | McKay ..................... 623/17.15 |
| 2007/0162000 A1* | 7/2007 | Perkins .......................... 606/61 |
| 2007/0173832 A1 | 7/2007 | Tebbe et al. |
| 2007/0198089 A1* | 8/2007 | Moskowitz et al. ....... 623/17.11 |
| 2008/0021466 A1* | 1/2008 | Shadduck et al. .............. 606/61 |
| 2009/0081602 A1* | 3/2009 | Ayan ................................ 433/7 |

* cited by examiner

SPINAL IMPLANT HAVING A POST-OPERATIVE ADJUSTABLE DIMENSION

FIELD OF THE INVENTION

The present invention relates generally to spinal implants and prostheses, and particularly to a spinal implant having a post-operative adjustable dimension.

BACKGROUND OF THE INVENTION

Spinal stenosis, as well as spondylosis, spondylolisthesis, osteoarthritis, scoliosis and other degenerative phenomena may be the cause of back pain, and may be caused by a narrowing of the spinal canal or foramina that result in stress acting on the spinal cord and/or nerve roots.

One of the methods for resolving back pain involves decompression, the removal of bony elements causing the pain, and fusion of two or more adjacent vertebrae. Unfortunately, fusion tends to have significant shortcoming and may cause the problem to migrate to adjacent vertebral components. Among the non-fusion solutions are disc replacement, dynamic stabilization systems and inter-spinous process implants.

Spinal implants with the capability of height adjustment are known. For example, U.S. Pat. Nos. 6,045,579, 6,080,193 and 6,576,016 to Hochshuler et al (issued Apr. 4, 200, Jun. 27, 2000 and Jun. 10, 2003, respectively) describe an adjustable height fusion device for promoting a spinal fusion between neighboring vertebrae. The device is located within the intervertebral disc space and includes a pair of engaging plates for contacting the vertebrae. An alignment device is used to alter the vertical distance between the engaging plates to customize the apparatus to fit a given patient. In one embodiment, the alignment device includes a pair of struts having a predetermined height and extending between the engaging plates from an anterior end to a posterior end of the apparatus. In another embodiment, the alignment device includes a rotatable connector and cam pins for adjusting the distance between the engaging plates. The alignment device is preferably adapted to vary the distance between the engaging plates such that the height of the apparatus proximate the anterior end is greater than that proximate the posterior end whereby the natural lordosis of the spine is maintained after the apparatus is installed.

However, these prior art devices must be adjusted prior to or during the installation and are not capable of post-operative adjustment.

SUMMARY OF THE INVENTION

The present invention seeks to provide an improved spinal implant (or prosthesis, the terms being used interchangeably) having a post-operative adjustable dimension, as described in more detail further below.

In one embodiment, at least one of its dimensions of the spinal implant can be modified post-implantation by means of remote control or a mechanical feature that can be connected to an adjustable portion of the implant, such as via a small puncture in the soft tissues. In one example, the adjustable portion (also referred to as a variable dimension mechanism) can have a piston-like configuration hydraulically or pneumatically activated by a small pressure tube. Other mechanical devices may be used and deployed, such as but not limited to, by a shaft, cable or other mechanical features. In another example, the adjustable portion can be electrically powered, such as by an electric motor (powered by electric cord, battery or remote induction), and controlled via remote control.

The prosthesis is configured to bridge between two vertebrae, most preferably but not limited to, adjacent vertebrae. The prosthesis includes a plurality of attachment members (end features) configured to be attached to a plurality of bone attachment points, such as but not limited to, spinous process, vertebral end plates or pedicles (via pedicle screws).

There is thus provided in accordance with a non-limiting embodiment of the present invention a spinal implant including first spinal attachment member for attaching to a first spinal portion, second spinal attachment member for attaching to a second spinal portion, and a post-implantation variable dimension device disposed between the first and second spinal attachment members, which is operable after completing surgery in which said spinal implant was installed into a patient, to cause relative movement between the first and second spinal attachment members.

In accordance with an embodiment of the present invention the first and second spinal attachment members include pedicle screws.

In accordance with an embodiment of the present invention the post-implantation variable dimension device changes a distance between the first and second spinal attachment members.

In accordance with an embodiment of the present invention the post-implantation variable dimension device changes a location of the first and second spinal attachment members both in vertical and sagittal planes.

In accordance with an embodiment of the present invention the first and second spinal attachment members include first and second support plates fitted with threaded shafts which are turned by a gear train, wherein rotation of the gear train changes a distance between the first and second support plates.

In accordance with an embodiment of the present invention the first and second spinal attachment members include first and second support plates inclined with respect to each other.

In accordance with an embodiment of the present invention the post-implantation variable dimension device is hydraulically or pneumatically operated.

In accordance with an embodiment of the present invention the post-implantation variable dimension device includes hinged arms which are pivotally connected to and moved by a screw mechanism.

In accordance with an embodiment of the present invention the post-implantation variable dimension device is electrically operated.

In accordance with an embodiment of the present invention the post-implantation variable dimension device includes an internal, implanted portion. The internal portion may include at least one of an electrical piston, an electric motor, a microprocessor, an RF emitter/transmitter, an LVDT, a strain sensor, an electric coil, a battery, and a capacitor.

In accordance with an embodiment of the present invention the post-implantation variable dimension device includes an external control portion. The external control portion may include at least one of a control panel, a processor, an RF transmitter/emitter, a magnetic power source, an electric coil and a cellular communication device. The communication between the external control portion and the implanted portion may be controlled by a code or password to protect against undesired operation of the internal device.

In accordance with an embodiment of the present invention the post-implantation variable dimension device is inflatable.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
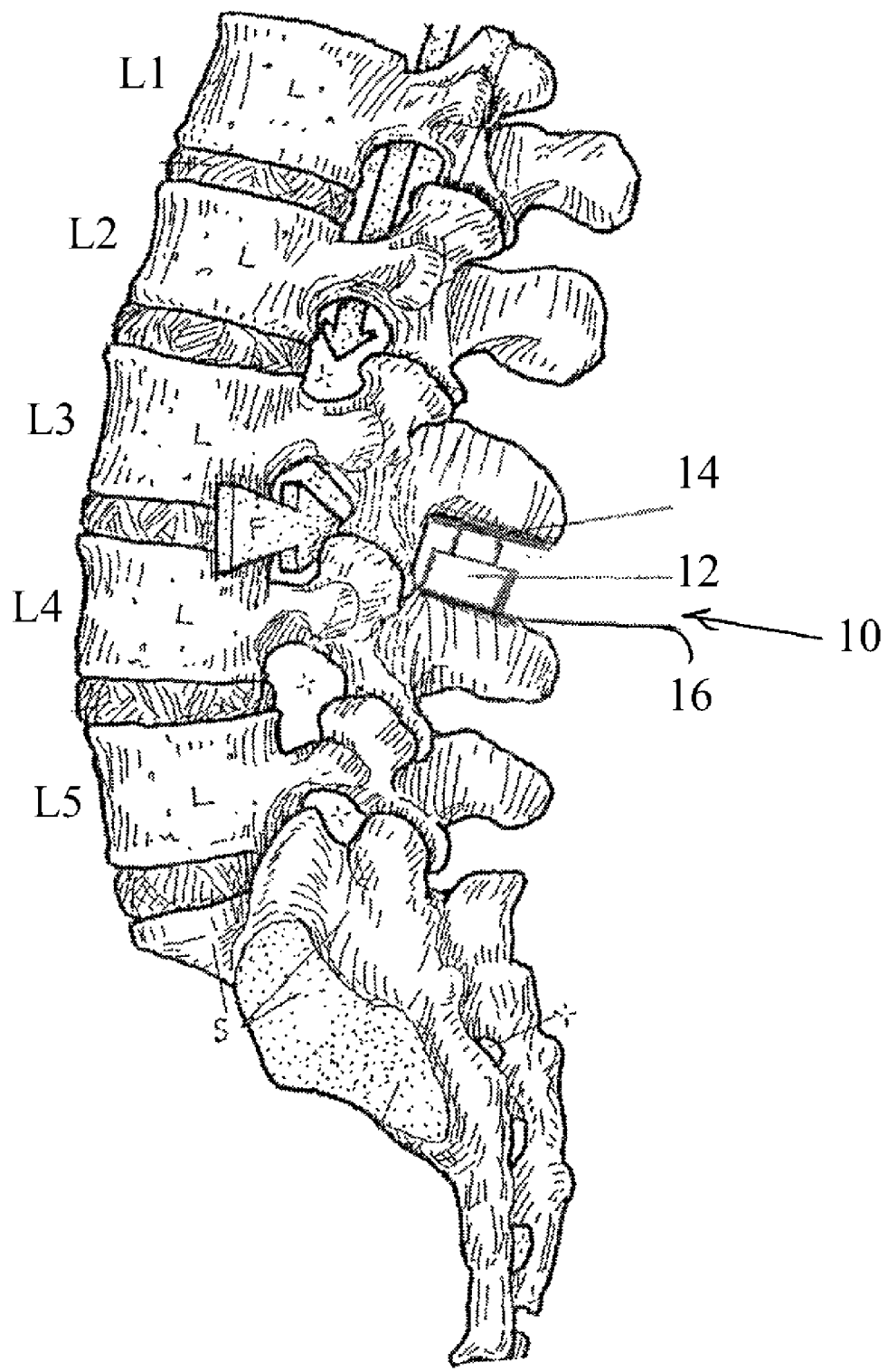
FIG. 1 is a simplified pictorial illustration of a spinal implant including a post-implantation variable dimension device, constructed and operative in accordance with an embodiment of the invention, implanted between two adjacent spinous processes.

Reference is now made to FIG. 1, which illustrates a spinal implant 10, constructed and operative in accordance with an embodiment of the invention.

Spinal implant 10 is shown implanted between two adjacent spinous processes of the lumbar spine (in this example, spinal implant 10 is an interspinous process device). Spinal implant 10 includes a post-implantation variable dimension device 12 disposed between a first (upper) support end plate (spinal attachment member) 14 and a second (lower) support end plate (spinal attachment member) 16. The post-implantation variable dimension device 12 may include a post arranged for linear motion (slightly tilted from vertical in the sense of the drawing), such as by means of a miniature linear actuator which is remote controlled. In general, post-implantation variable dimension device 12 may be constructed in accordance with any of the embodiments described below with reference to FIGS. 6-9.

Figure 2:
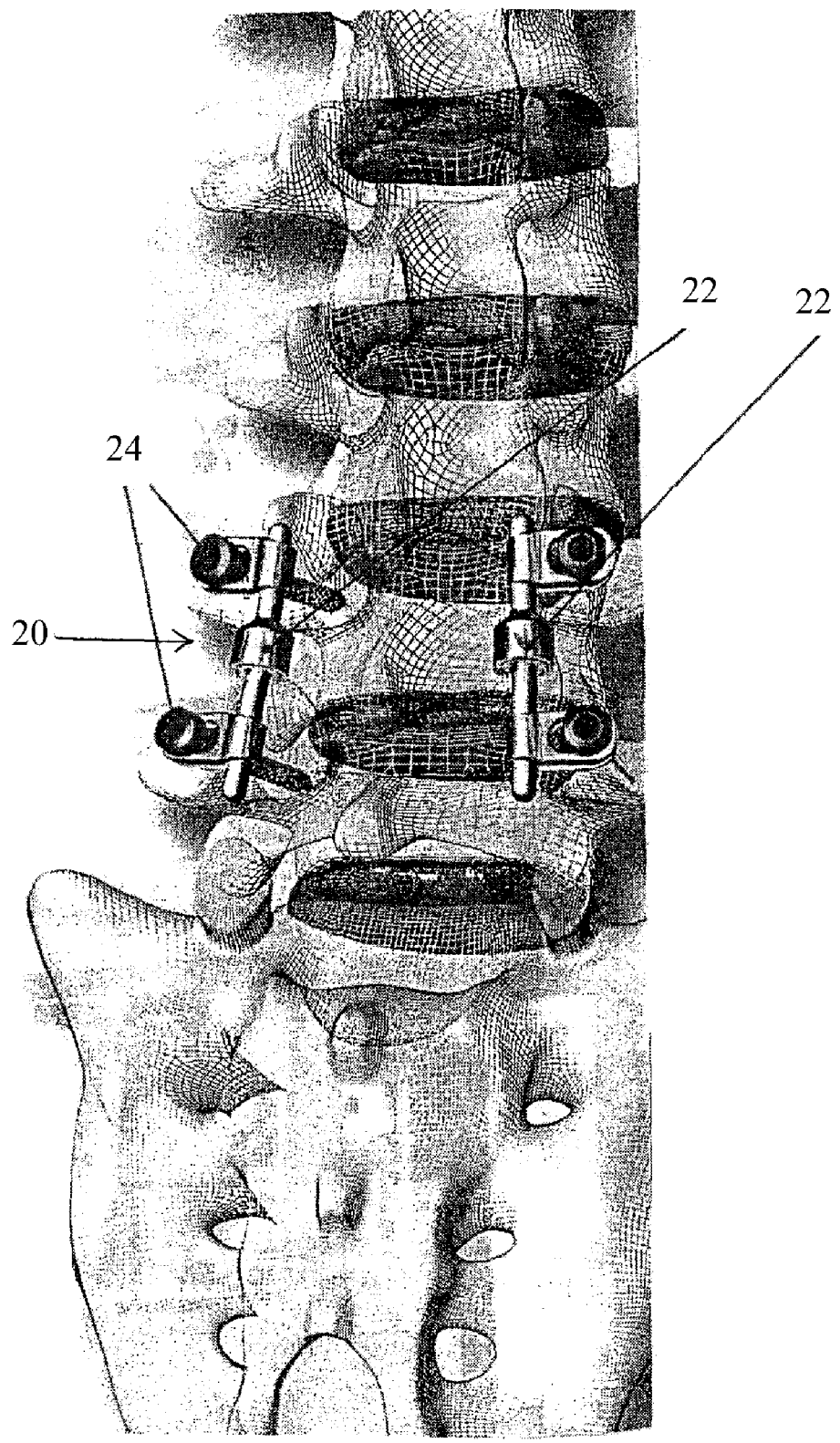
FIG. 2 is a simplified pictorial illustration of a spinal implant including a post-implantation variable dimension device, constructed and operative in accordance with another embodiment of the invention, connected to pedicle screws so that actuating the variable dimension mechanism can change the distance between the screws.

Reference is now made to FIG. 2, which illustrates a spinal implant 20, constructed and operative in accordance with another embodiment of the invention. Spinal implant 20 includes a post-implantation variable dimension device 22, and is connected to pedicle screws 24 (spinal attachment members 24). Actuation of variable dimension device 22 changes the distance between screws 24. Here too, post-implantation variable dimension device 22 may include a post arranged for linear motion, such as by means of a miniature linear actuator which is remote controlled. In general, post-implantation variable dimension device 22 may be constructed in accordance with any of the embodiments described below with reference to FIGS. 6-9.

Figure 3:
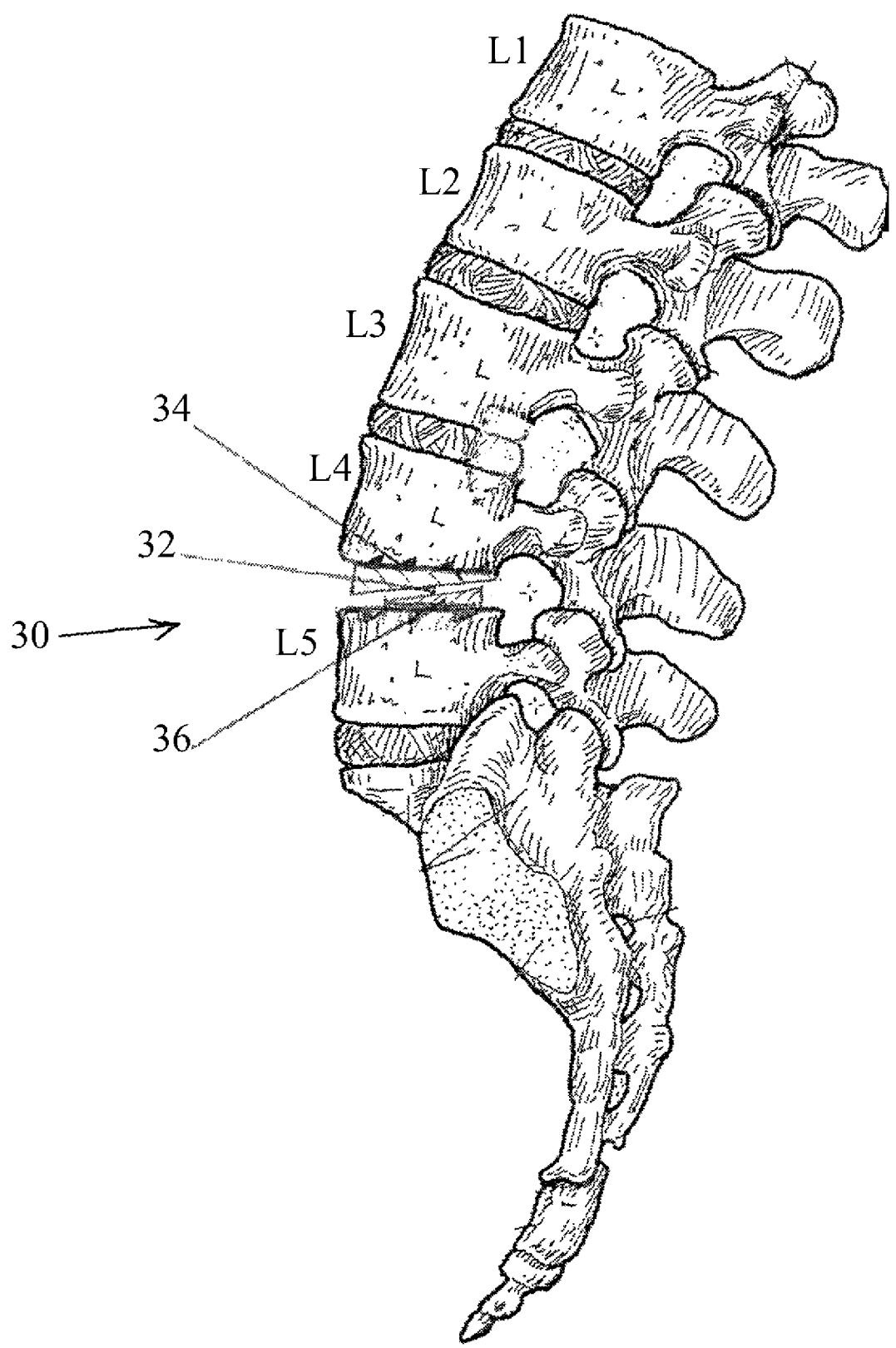
FIG. 3 is a simplified pictorial illustration of a spinal implant including a post-implantation variable dimension device, constructed and operative in accordance with yet another embodiment of the invention, inserted in between two adjacent vertebrae.

Reference is now made to FIG. 3, which illustrates a spinal implant 30 including a post-implantation variable dimension device 32, constructed and operative in accordance with yet another embodiment of the invention, inserted in between two adjacent vertebrae (e.g., L4 and L5). Spinal implant 30 includes a first (upper) support plate 34 connected to and supporting an upper vertebra, and a second (lower) support plate 36 connected to and supporting a lower vertebra. The variable dimension device 32 is installed between first and second support plates (spinal attachment members) 34 and 36. Actuation of variable dimension device 32 changes the distance between first and second support plates 34 and 36, and can change the location between the two adjacent vertebrae both in the vertical and the sagittal planes. The post-implantation variable dimension device 32 may be constructed in accordance with the embodiment described below with reference to FIG. 5.

Figure 4:
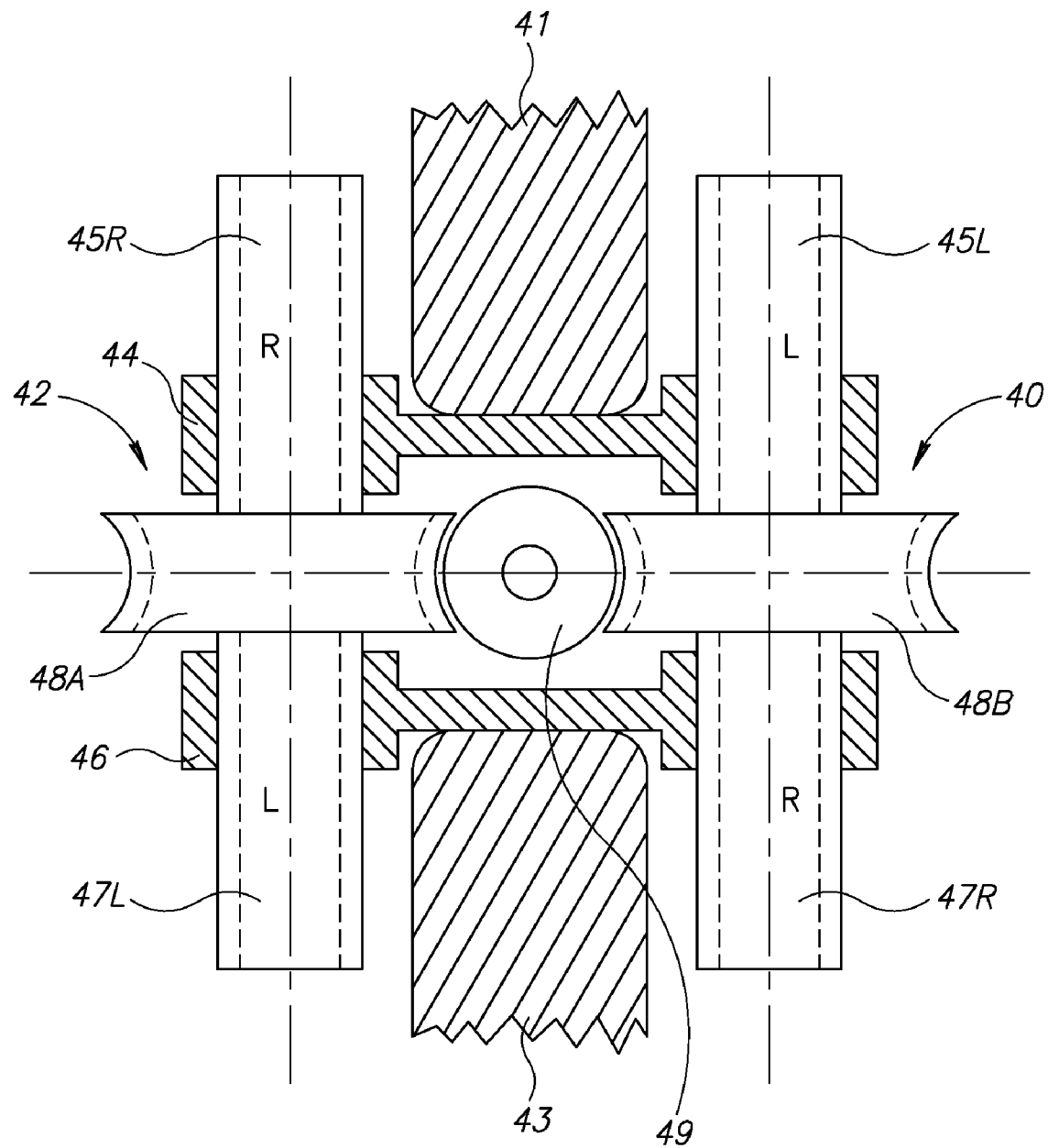
FIG. 4 is a simplified pictorial illustration of a spinal implant including a post-implantation variable dimension device, constructed and operative in accordance with still another embodiment of the invention, used to create an optimal distraction between two adjacent spinous processes.

Reference is now made to FIG. 4, which illustrates a spinal implant 40 including a post-implantation variable dimension device 42, constructed and operative in accordance with still another embodiment of the invention. Implant 40 can be used to create an optimal distraction between two adjacent spinous processes, such as the superior spinous process 41 and inferior spinous process 43.

Spinal implant 40 includes first and second support plates (spinal attachment member) 44 and 46 that respectively support the superior spinous process 41 and inferior spinous process 43. First and second support plates 44 and 46 are each tapped with threaded holes to accept threaded shafts 45L and 45R, and 47L and 47R, respectively. Threaded shafts 45L and 47L have left-handed threads, while threaded shafts 45R and 47R have right-handed threads.

Gear pulleys 48A and 48B are connected to threaded shafts 45L, 45R, 47L and 47R, and are driven by a worm gear 49. Rotation of worm gear 49 changes the distance between first and second support plates 44 and 46 and the supported spinous processes.

Figure 5:
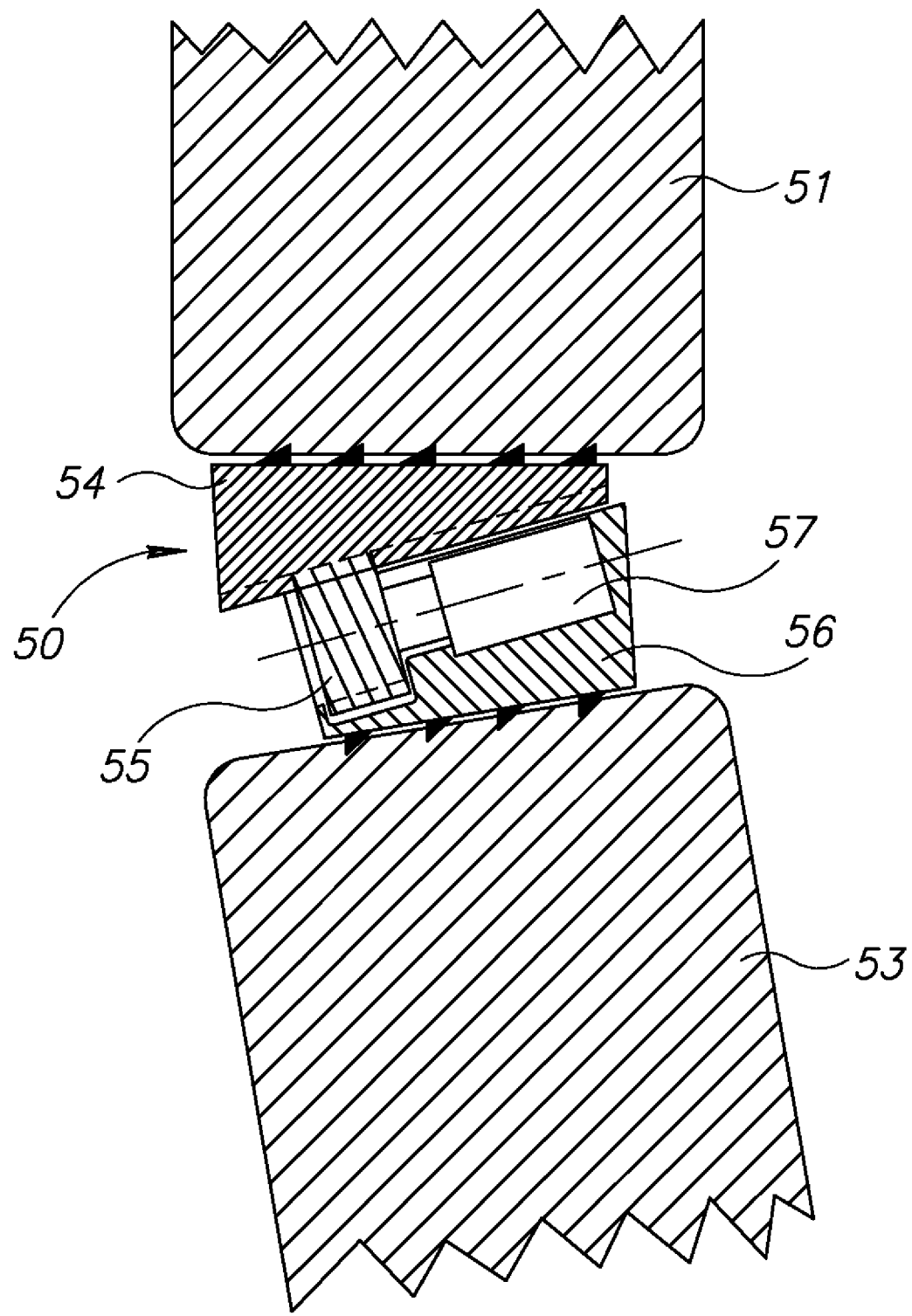
FIG. 5 is a simplified pictorial illustration of a spinal implant including a post-implantation variable dimension device, constructed and operative in accordance with yet another embodiment of the invention, used to change the location of adjacent vertebrae.

Reference is now made to FIG. 5, which illustrates a spinal implant 50 including a post-implantation variable dimension device 52, constructed and operative in accordance with yet another embodiment of the invention.

Spinal implant 50 may be used to change the location of adjacent vertebrae 51 and 53. Spinal implant 50 includes a first (upper) support plate 54 having a threaded slot in which a threaded screw 55 is threadedly received. Spinal implant 50 includes a second (lower) support plate 56 that includes a recess in which an electrical motor (or actuator) 57 is mounted. The electrical motor 57 (which may be remote controlled) turns screw 55, which causes first support plate 54 to slide with respect to second support plate 56. The inclined mating between first and second support plates (spinal attachment members) 54 and 56 causes a change in the adjacent location between the two vertebras, both in the vertical and the sagittal planes.

Figure 6:
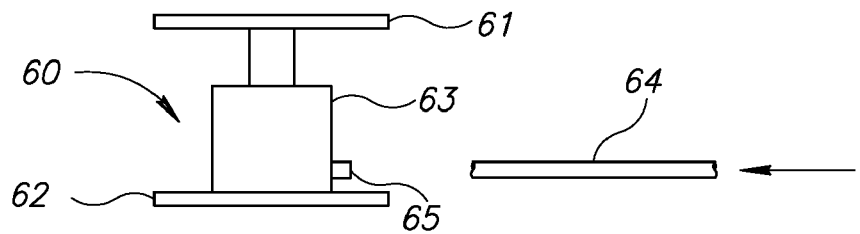
FIG. 6 is a simplified pictorial illustration of a hydraulically or pneumatically operated post-implantation variable dimension device, constructed and operative in accordance with an embodiment of the invention.

Reference is now made to FIG. 6, which illustrates a hydraulically or pneumatically operated post-implantation variable dimension device 60, constructed and operative in accordance with an embodiment of the invention. Variable dimension device 60 includes two end plates (spinal attachment members) 61 and 62, both attached to a piston 63. Piston 63 is fluidly actuated (that is, either hydraulically or pneumatically), such as by means of compressed liquid (e.g., water) or gas (e.g., air). The compressed fluid is introduced to piston 63 by means of a tube 64 which is connected to a fluid inlet 65.

Figure 7:
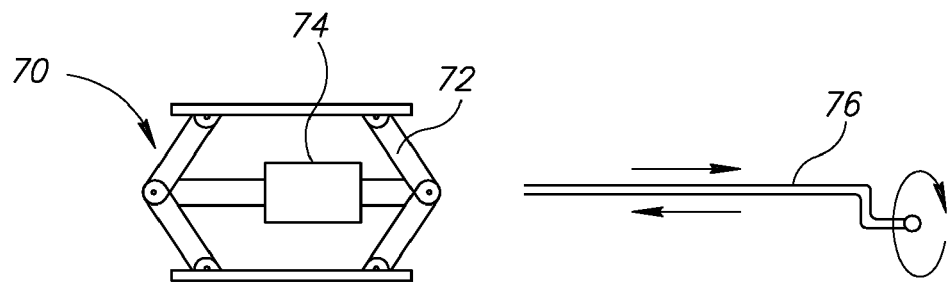
FIG. 7 is a simplified pictorial illustration of a mechanically operated post-implantation variable dimension device, constructed and operative in accordance with an embodiment of the invention.

Reference is now made to FIG. 7, which illustrates a mechanically operated post-implantation variable dimension device 70, constructed and operative in accordance with an embodiment of the invention. Variable dimension device 70 includes hinged arms 72 which are pivotally connected to and moved by a male/female screw mechanism 74 operated by a turn-handle 76.

Figure 8:
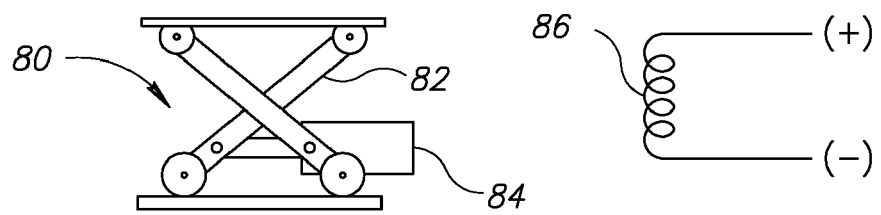
FIG. 8 is a simplified pictorial illustration of an electrically operated post-implantation variable dimension device, constructed and operative in accordance with an embodiment of the invention.

Reference is now made to FIG. 8, which illustrates an electrically operated post-implantation variable dimension device 80, constructed and operative in accordance with an embodiment of the invention. Variable dimension device 80 includes hinged arms 82 which are pivotally connected to and moved by an electrical piston (electrical actuator or solenoid) 84, which may be externally operated by an inductance coil 86.

The electrically operated post-implantation variable dimension device 80 may have an internal, implanted portion and/or an external, control portion. The internal portion may include, without limitation, electrical piston 84, an electric motor, microprocessor, RF emitter/transmitter, LVDT (linear variable differential transducer), strain sensor, electric coil for direct energy transfer into the motor from an external coil, battery, capacitor to accumulate energy, or any combination thereof.

The external portion may include, without limitation, a control panel, processor, RF transmitter/emitter, magnetic power source, electric coil to transfer energy to the internal unit, or any combination thereof. The external portion may also include a cellular communication device to allow remote control by the physician. A code or password may be incorporated into the control system to prevent unwanted operation.

Figure 9:
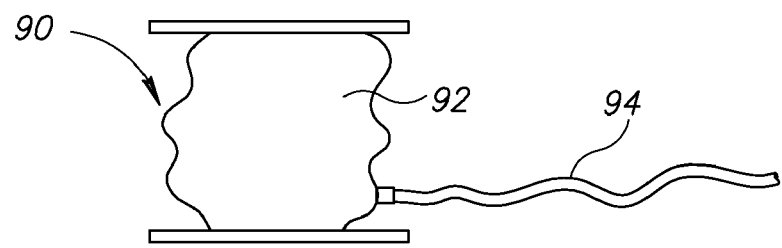
FIG. 9 is a simplified pictorial illustration of an inflatable post-implantation variable dimension device, constructed and operative in accordance with an embodiment of the invention.

Reference is now made to FIG. 9, which illustrates an inflatable post-implantation variable dimension device 90, constructed and operative in accordance with an embodiment of the invention. Variable dimension device 90 includes an inflatable pillow or cushion 92 inflatable via a small tube 94.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A spinal implant for causing distraction between a superior spinous process and an inferior spinous process in a body, the implant comprising:
   a first support plate for positioning inferiorly to the superior spinous process;
   a second support plate for positioning superiorly to the inferior spinous process; and
   a post-implantation variable dimension device disposed between said first and second support plates, which is operable after implanting said spinal implant into a patient, wherein said post-implantation variable dimension device comprises parallel threaded shafts, each of said shafts passing through each of said support plates, and said shafts being turned by a gear train, wherein rotation of said gear train causes said first support plate to push against the superior spinous process in a superior direction and said second support plate to push against the inferior spinous process in an inferior direction and changes a distance between said first and second support plates.

2. The spinal implant according to claim 1, wherein said gear train meshes with left and right threaded shafts, left and right being defined as left and right of a sagittal plane of the body, and said gear train is driven by a gear which is rotated about a rotational axis lying in the sagittal plane.

3. The spinal implant according to claim 2, wherein the rotational axis is collinear with an anterior-posterior axis of the body.

4. The spinal implant according to claim 2, wherein said gear train meshes with gears mounted on said left and right threaded shafts, said gears being larger in diameter than said left and right threaded shafts.

* * * * *